(12) United States Patent
Miyazaki (10) Patent No.: US 11,103,300 B2
(45) Date of Patent: Aug. 31, 2021

(54) MEDICAL MEMBER AND MEDICAL DEVICE

(71) Applicant: OLYMPUS CORPORATION, Hachioji (JP)

(72) Inventor: Akira Miyazaki, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 853 days.

(21) Appl. No.: 15/837,219

(22) Filed: Dec. 11, 2017

(65) Prior Publication Data

US 2018/0098809 A1 Apr. 12, 2018

Related U.S. Application Data

(63) Continuation of application No. PCT/JP2016/066928, filed on Jun. 7, 2016.

(30) Foreign Application Priority Data

Jun. 25, 2015 (JP) .............................. JP2015-127765

(51) Int. Cl.
*A61B 18/14* (2006.01)
*A61B 17/32* (2006.01)
(Continued)

(52) U.S. Cl.
CPC .. *A61B 18/1442* (2013.01); *A61B 17/320092* (2013.01); *A61B 17/2812* (2013.01);
(Continued)

(58) Field of Classification Search
CPC ...... A61B 18/1442; A61B 2018/00077; A61B 2018/0083; A61B 2018/00101;
(Continued)

(56) References Cited

U.S. PATENT DOCUMENTS 5,482,054 A * 1/1996 Slater .................. A61M 1/0064
600/564
6,041,679 A * 3/2000 Slater ................. A61B 17/1608
76/104.1
(Continued)

FOREIGN PATENT DOCUMENTS

| JP | 2005-193061 A | 7/2005 |
| JP | 2008-246222 A | 10/2008 |
| JP | 2014-121618 A | 7/2014 |

OTHER PUBLICATIONS

Aug. 2, 2016 International Search Report issued in International Patent Application No. PCT/JP2016/066928.
(Continued)

*Primary Examiner* — Ronald Hupczey, Jr.
(74) *Attorney, Agent, or Firm* — Oliff PLC (57) ABSTRACT

A medical member improved in yield is provided.
The medical member is assembled with an assembly unit, is movable relative to at least part of the assembly unit, and is provided with: a conductor including a plurality of curved portions and a through hole extending along a plane including the plurality of curved portions; and a coating portion integrally formed with the conductor in such a manner as to cover the periphery of the conductor and fill the interior of the through hole.

13 Claims, 5 Drawing Sheets

(51) Int. Cl.
- *A61B 17/29* (2006.01)
- *A61B 17/28* (2006.01)
- *A61B 90/00* (2016.01)
- *A61B 18/00* (2006.01)

(52) U.S. Cl.
CPC .......... *A61B 2017/2825* (2013.01); *A61B 2017/2926* (2013.01); *A61B 2017/2947* (2013.01); *A61B 2017/320082* (2017.08); *A61B 2017/320094* (2017.08); *A61B 2017/320095* (2017.08); *A61B 2018/0063* (2013.01); *A61B 2018/00077* (2013.01); *A61B 2018/00083* (2013.01); *A61B 2018/00101* (2013.01); *A61B 2018/00589* (2013.01); *A61B 2018/00994* (2013.01); *A61B 2090/033* (2016.02)

(58) Field of Classification Search
CPC .. A61B 2018/00589; A61B 2018/0063; A61B 2018/00994; A61B 17/2812; A61B 17/320092; A61B 2017/320082; A61B 2017/320094; A61B 2017/320095; A61B 2017/2825; A61B 2017/2926; A61B 2017/2947; A61B 2090/033

See application file for complete search history.

(56) References Cited

U.S. PATENT DOCUMENTS

| | | |
|---|---|---|
| 2006/0259054 A1 | 11/2006 | Masuda et al. |
| 2013/0303949 A1 | 11/2013 | Kawaguchi et al. |

OTHER PUBLICATIONS

Dec. 26, 2017 International Preliminary Report on Patentability issued in International Patent Application No. PCT/JP2016/066928.

Feb. 14, 2017 Office Action issued in Japanese Patent Application No. 2017-501343.

* cited by examiner

MEDICAL MEMBER AND MEDICAL DEVICE

CROSS-REFERENCE TO RELATED APPLICATIONS

This application is a Continuation Application of PCT Application No. PCT/JP2016/066928, filed Jun. 7, 2016 and based upon and claiming the benefit of priority from prior Japanese Patent Application No. 2015-127765, filed Jun. 25, 2015, the entire contents of all of which are incorporated herein by reference.

BACKGROUND OF THE INVENTION

1. Field of the Invention

The present invention relates to a medical member for use in a medical device with which to treat an object to be treated.

2. Description of the Related Art

An endoscopic biopsy forceps device is disclosed in Jpn. Pat. Appln. KOKAI No. 2005-193061 (patent literature 1). This ultrasonic treatment device includes opposed jaws, and the opposed jaws can be coupled to an electric cauterization power supply through a wire.

BRIEF SUMMARY OF THE INVENTION

A medical member according to an embodiment of the present invention is assembled with an assembly unit, is movable relative to at least part of the assembly unit, and is provided with: a conductor extending along a plane including a plurality of curved portions and a through hole extending along a plane including the plurality of curved portions; and a coating portion integrally formed with the conductor in such a manner as to cover the periphery of the conductor and fill the interior of the through hole.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

A medical device of the first embodiment of the present invention will be described with reference to FIGS. 1 to 7.

Figure 1:
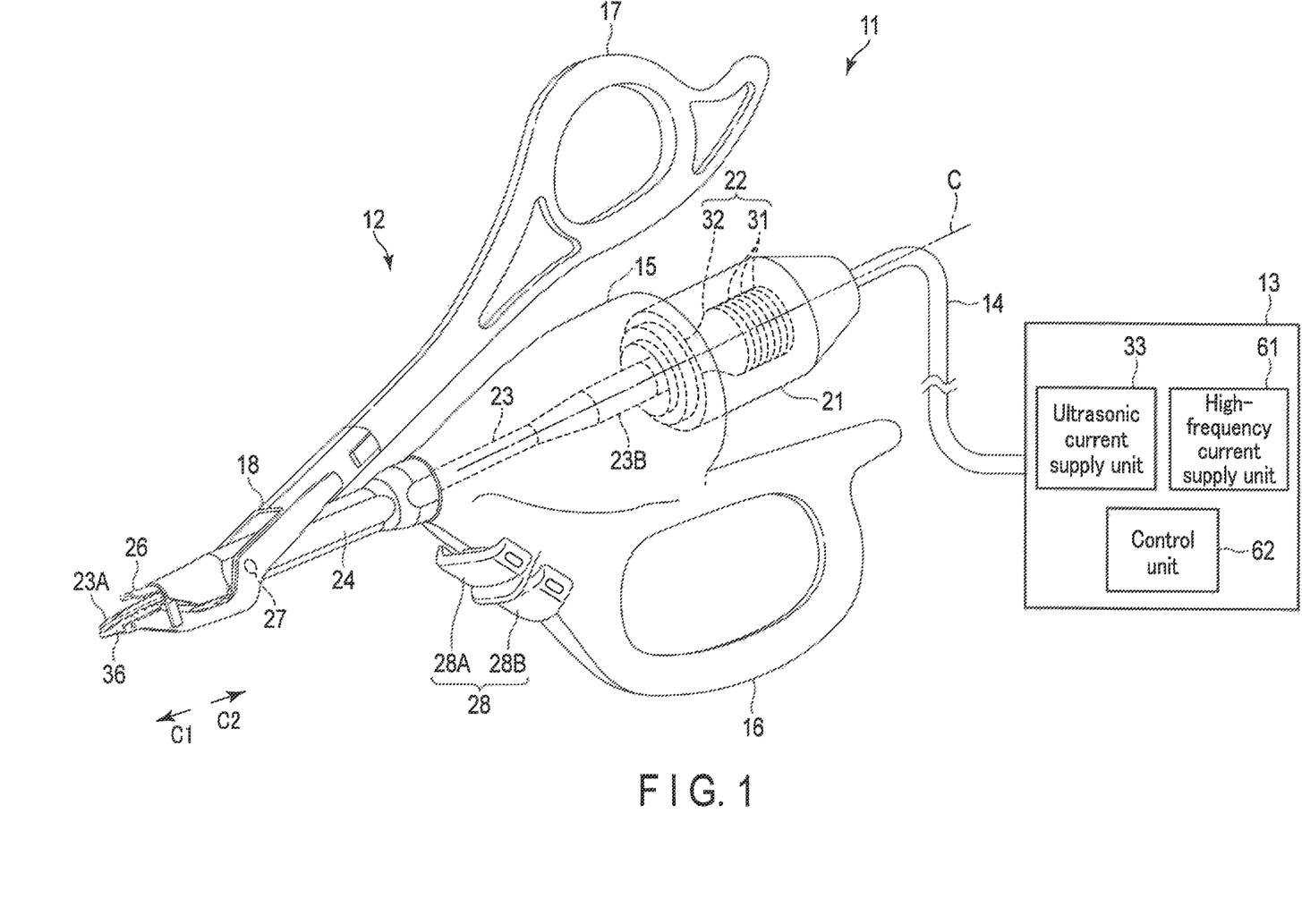
FIG. 1 is a schematic diagram showing the entire structure of a medical device according to the first embodiment.

As shown in FIG. 1, a treatment device 11, an example of a medical device, is provided with a hand piece 12, a power supply unit 13, and a cable 14 for connecting the hand piece 12 and the power supply unit 13.

Figure 2:
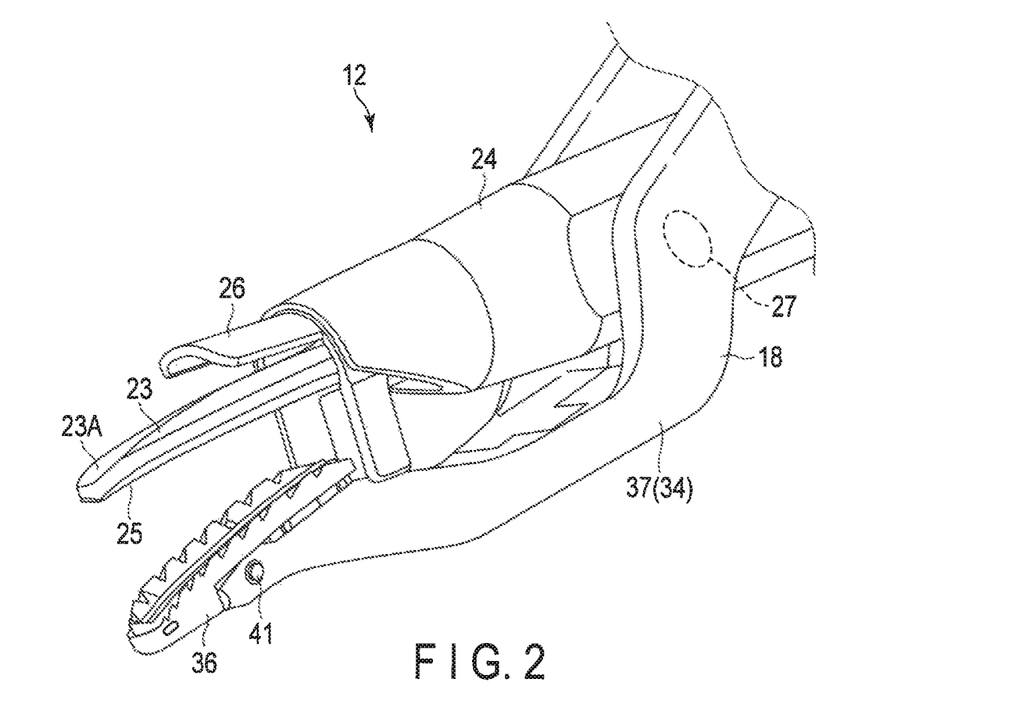
FIG. 2 is a perspective view showing the distal end portion of the vibration transmission member of the medical device depicted in FIG. 1 and jaw of a clamp arm.
Figure 3:
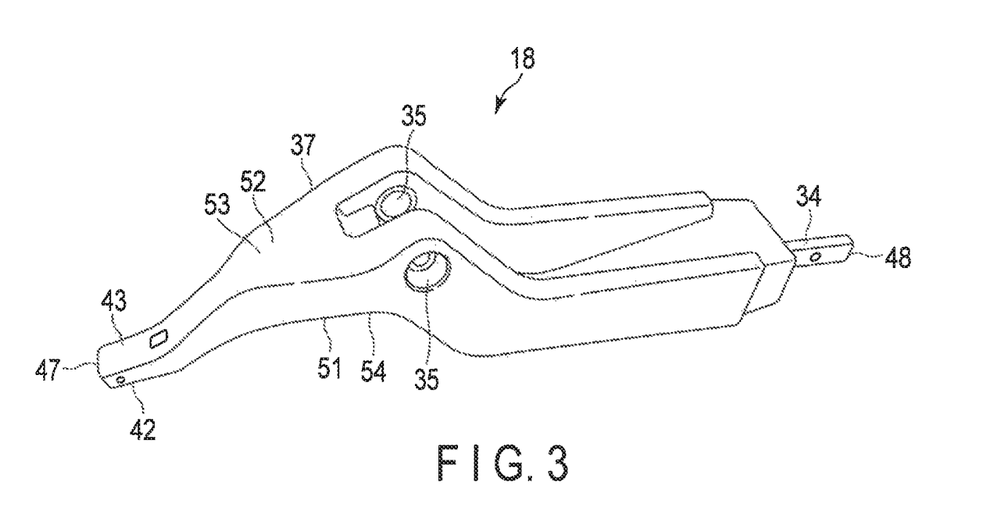
FIG. 3 is a perspective view showing the clamp arm of the medical device depicted in FIG. 1.

As shown in FIGS. 1 to 3, the hand piece 12 (assembly unit) is provided with: a resin housing 15 constituting an outer shell; a fixed handle 16 fixed to the housing 15; a movable handle 17 movable relative to the housing 15; a clamp arm 18 provided on the distal side of the movable handle 17 and being movable together with the movable handle 17; a case 21 detachably attached to the housing 15; a vibration generator 22 (transducer) stored in the case 21; a rod-like vibration transmission member 23 (shaft unit; probe) connected to the vibration generator 22; a cylindrical sheath 24 covering the periphery of the vibration transmission member 23 and protecting the vibration transmission member 23; a resin cover 26 for covering the back surface opposite to the treatment surface 25 of the vibration transmission member 23; a shaft 27 for attaching the clamp arm 18 to the sheath 24; and a plurality of operation buttons 28 provided on the housing 15. In the present embodiment, one of the two directions parallel to the longitudinal direction C of the vibration transmission member 23 will be referred to as distal direction C1, and the direction opposite to the distal direction C1 will be referred to as proximal direction C2. The clamp arm 18 is an example of a medical member.

In the present embodiment, the number of operation buttons 28 is two. A first operation button 28A corresponds to the so-called coagulation mode and is operated when ultrasonic energy and high-frequency energy suitable for the coagulation of a living tissue and the sealing of a blood vessel are to be output. A second operation button 28B corresponds to the so-called coagulation-incision mode and is operated when ultrasonic energy and high-frequency energy suitable for the coagulation and incision of a living tissue and the sealing and incision of a blood vessel are to be output.

As shown in FIG. 1, the vibration generator 22 is provided with an ultrasonic transducer 31 and a horn member 32. The ultrasonic transducer 31 includes a plurality of piezoelectric elements for converting a current into ultrasonic vibration. One end of an electric wiring line is connected to the ultrasonic transducer 31. The electric line passes through the interior of a cable 14 and is connected, at the other end, to the ultrasonic current supply unit 33 (ultrasonic energy generator) of the power supply unit 13. When power is supplied from the ultrasonic current supply unit 33 to the ultrasonic transducer 31 through the electric wiring line, the ultrasonic transducer 31 generates ultrasonic vibration.

As shown in FIG. 1, the ultrasonic transducer 31 is attached to the horn member 32. The horn member 32 is made of a metallic material. The horn member 32 includes a substantially cylindrical cross-section changing portion whose cross sectional area decreases in the distal direction C1 of the vibration transmission member 23. The amplitude of the ultrasonic vibration generated by the ultrasonic transducer 31 increases in the cross-section changing portion.

As shown in FIG. 2, the vibration transmission member 23 is a rod-like member made, for example, of a biocompatible material (e.g., a titanium alloy). Ultrasonic vibration used for treatment can be transmitted to the vibration transmission member 23. The vibration transmission member 23 includes a distal end portion 23A provided at the distal direction (C1) side of the longitudinal direction C and constituting a treatment surface 25, and a proximal end portion 23B provided on the opposed side of the distal end portion 23A. The proximal end portion 23B is connected to one of two second electric wiring lines. The vibration transmission member 23 receives ultrasonic vibration transmitted from the vibration generator 22 and also receives a high-frequency current supplied from a high-frequency current supply unit 61. Therefore, the vibration transmission member 23 (shaft unit) not only applies ultrasonic vibration to a living tissue but also serves as one pole of the bipolar electrode used for bipolar treatment.

The shaft 27 is formed of a conductive metal and shaped like a pin. The proximal portion of the shaft 27 is fitted in a conduction hole 35 (mentioned later) of the clamp arm 18. As shown in FIG. 2 etc., the shaft 27 can support the clamp arm 18 such that it is movable relative to sheath 24 and the housing 15. In other words, the distal end portion of the shaft 27 is pivotally fitted in a depression formed in the sheath 24. A conductor 34 of the clamp arm 18 is electrically connected to the sheath 24 by way of the shaft 27 and the conduction hole 35.

The proximal end portion of the sheath 24 is connected to the other one of the two second electric wiring lines. A jaw 36 (mentioned later) of the clamp arm 18 is electrically connected to the sheath 24 by way of the shaft 27 mentioned above and the conductor 34 mentioned later. With this structure, the jaw 36 and the conductor 34 supporting the jaw 36 jointly serve as the other pole of the bipolar electrode for bipolar treatment. The electrode portion of the jaw 36 is formed, for example, of a copper alloy or the like.

As shown in FIG. 1 to FIG. 3, the clamp arm 18 is an example of a medical member which can be used as a part constituting the treatment device 11. The clamp arm 18 includes: the conductor 34 formed of a conductive metal and shaped substantially like a rod having a curved portion at a halfway position; a coating portion 37 formed integrally with the conductor 34 in such a manner as to cover the surface of the conductor 34 (the whole periphery except for a certain portion); a grasping surface 42 provided at the distal end portion of the conductor 34; and a jaw 36 fixed to the grasping surface 42 by mean of a pin 41.

As shown in FIG. 3, the coating portion 37 is integral with the conductor 34 and made by insert molding, by which the conductor 34 is inserted. In the neighborhood of the conductor 34, the coating portion 37 covers an opposite surface 43, which is provided opposite to the grasping surface 42 mentioned later. The coating portion 37 fills the interior of a first through hole 44, a second through hole 45 and auxiliary through holes 46 (to be described later) of the conductor 34. The coating portion 37 covers those portions (mentioned later) which are away from the conduction hole 35 of the conductor 34. The coating portion 37 is made, for example, of resin (synthetic resin) having electrical insulation property and heat insulation property. The coating portion 37 may be made of PEEK, for example, but may be made of another kind of synthetic resin. The heat insulation property mentioned here means that the coefficient of thermal conductivity is sufficiently smaller than that of the conductor 34 (metal) or the like.

The jaw 36 is fixed to the grasping surface 42 by means of a pin 41 and is swingable relative to a base member, with the pin 41 as a fulcrum. The jaw 36 has a contact surface which is depressed in accordance with the projection of the treatment surface 25 of the vibration transmission member 23. The contact surface of the jaw 36 can be brought into engagement with the treatment surface 25.

As shown in FIGS. 4 to 7, the conductor 34 is an integral member made of stainless steel, for example. The conductor 34 may be made of a copper alloy, an aluminum alloy or another kind of conductive metal.

The conductor 34 includes: a distal end portion 47; a proximal end portion 48 opposite to the distal end portion 47; a grasping surface 42 formed on the distal end portion (47) side, brought into contact with a living tissue by means of the jaw 36 and serving to grasp the living tissue; a first surface 51 including the grasping surface 42; a second surface 52 provided on the opposite side of the first surface 51; a first curved portion 53 provided on the distal end portion (47) side; a second curved portion 54 provided on the proximal end portion (48) side; an opening 55 provided (at the boundary) between the first curved portion 53 and the second curved portion 54; a pair of side wall portions 56 provided in such a manner as to cover the first curved portion 53, the opening 55 and the second curved portion 54; conduction holes 35 (conduction hole portions) penetrating the side wall portions 56; a first through hole 44 (first through hole portion) penetrating the first curved portion 53; and a second through hole 45 (second through hole portion) penetrating the second curved portion 54.

Figure 6:
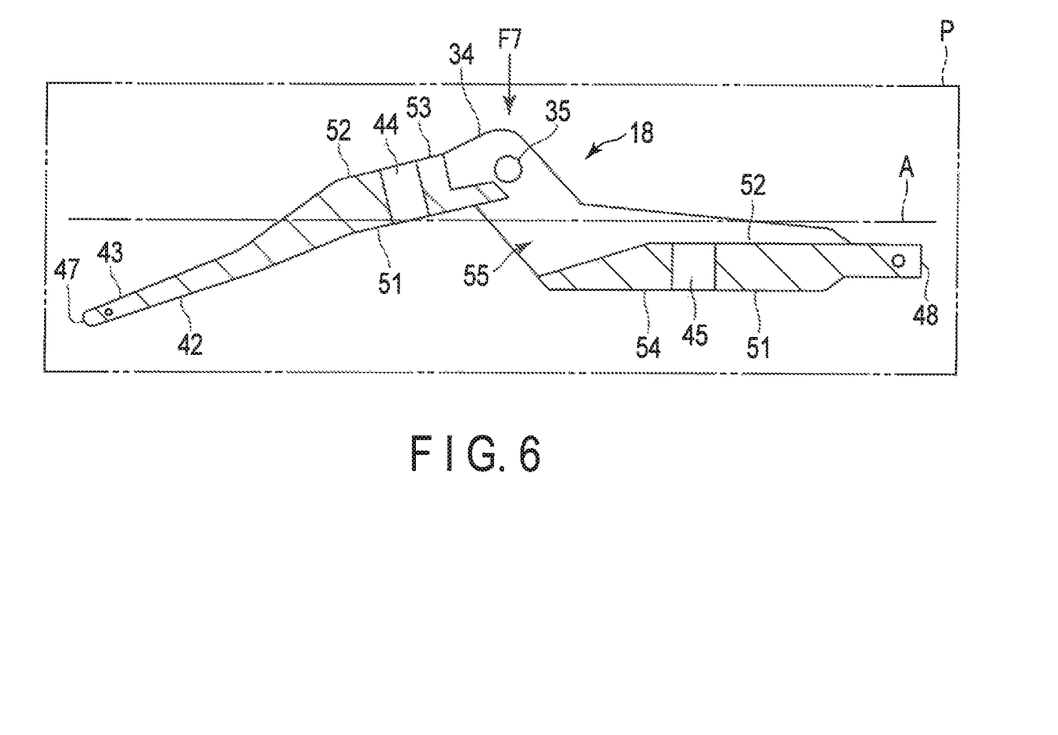
FIG. 6 is a sectional view showing how the conductor depicted in FIG. 4 is when it is taken along a plane including both the first and second curved portions of the conductor.
Figure 7:
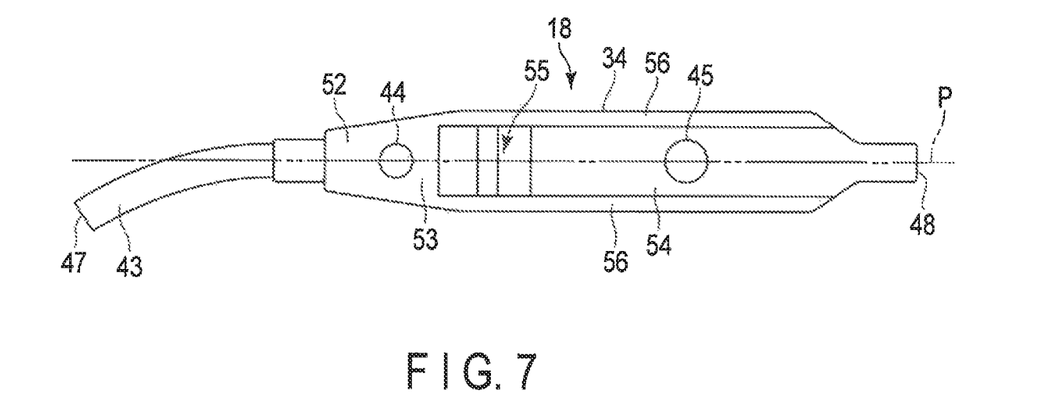
FIG. 7 is a plan view showing how the conductor depicted in FIG. 6 looks like when viewed in the direction of arrow A of FIG. 6.

The distal end portion 47 is shaped substantially like "J" such that it conforms with the curve of the treatment surface 25 of the vibration transmission member 23. The first through hole 44 penetrates the first curved portion 53 (first positional shift portion) in the thickness direction thereof and therefore penetrates the first surface 51 and the second surface 52. The second through hole 45 penetrates the second curved portion 54 (second positional shift portion) in the thickness direction thereof and therefore penetrates the first surface 51 and the second surface 52. As shown in FIG. 6, the first through hole 44 and the second through hole 45 extend along plane P including both the first curved portion 53 and the second curved portion 54.

As shown in FIG. 6, the first curved portion 53 (first positional shift portion) and the second curved portion 54 (second positional shift portion) are shifted from the central axis (reference line) of the conductor 34. The first curved portion 53 and the second curved portion 54 are portions by which the rigidity of the clamp arm 18 is ensured. The first curved portion 53 and the second curved portion 54 extend along the central axis A. In the present embodiment, the expression "along the central axis A" is intended to mean both being substantially parallel to the central axis A and being slightly slanted with respect to the central axis A. In the present embodiment, as shown in FIG. 6, the first curved portion 53 is slightly oblique with respect to the central axis A, and the second curved portion 54 is substantially parallel to the central axis A. The first curved portion 53 and the second curved portion 54 are asymmetric portions which are asymmetric with respect to the central axis A. The sheath 24 can be passed through the opening 55.

Figure 4:
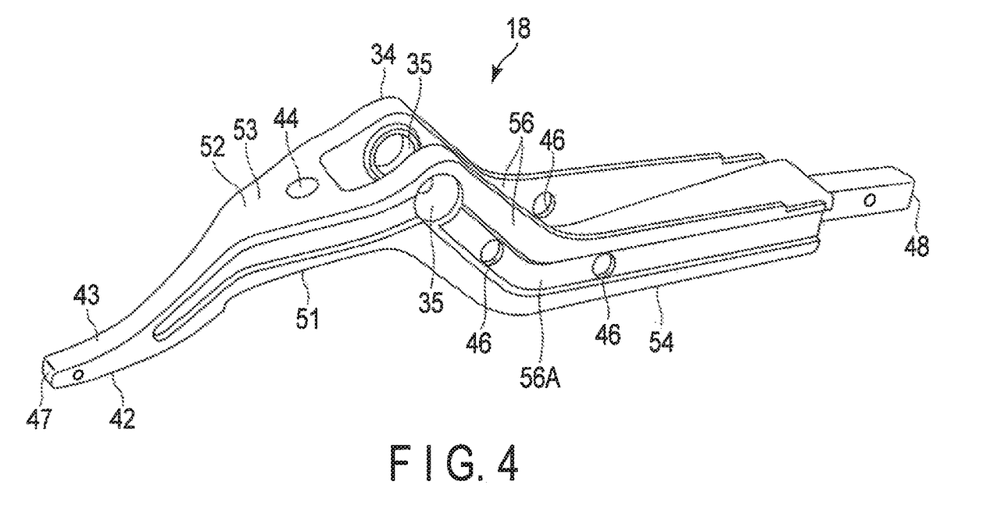
FIG. 4 is a perspective view showing the conductor of the clamp arm depicted in FIG. 3.
Figure 5:
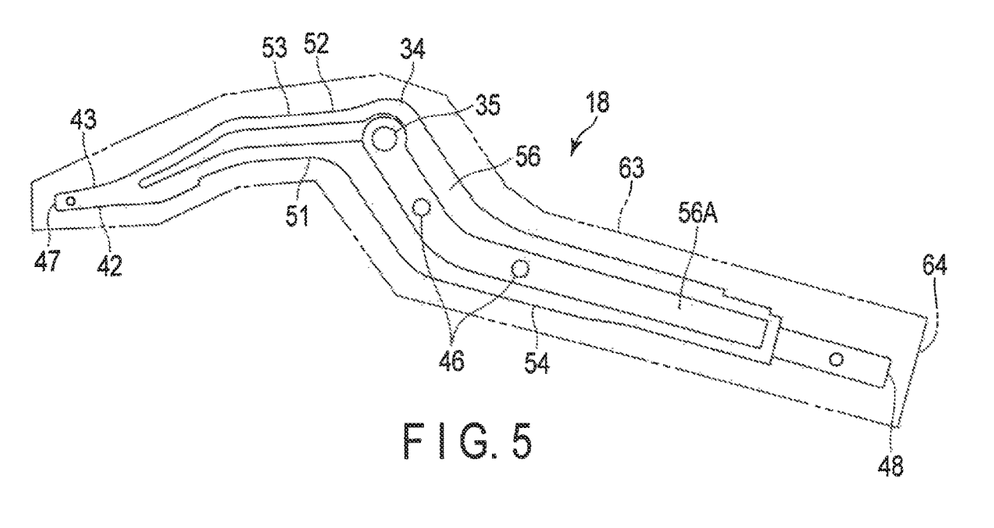
FIG. 5 is a side view showing how the conductor depicted in FIG. 4 looks like when viewed sideways.

As shown in FIGS. 4 and 5, the side wall portions 56 are provided to extend from the distal end portion 47 to the proximal end portion 48. The side wall portions 56 are provided with depressed portions 56A extending in such a manner as to cover the positions of the first curved portion 53, opening 55 and second curved portion. The depressed portions 56A are continuously provided from the distal end portion 47 to the proximal end portion 48. The conduction holes 35 and a plurality of (two) auxiliary through holes 46 (auxiliary through hole portions), by which the molten resin (coating portion 37) can easily flow at the time of molding, are provided at the corresponding positions of the depressed portions 56A of the side wall portions 56. The auxiliary through holes 46 penetrate the respective side wall portions 56.

As shown in FIG. 6, the first through hole 44 penetrates both the first surface 51 and the second surface 52 in the first curved portion 53. The second through hole 45 penetrates both the first surface 51 and the second surface 52 in the second curved portion 54. The first through hole 44 and the second through hole 45 extend in directions intersecting the central axis A (reference line). The first through hole 44 and the second through hole 45 extend in directions intersecting the conduction holes 35.

As shown in FIG. 1, the power supply unit 13 includes an ultrasonic current supply unit 33 (ultrasonic energy supply unit), a high-frequency current supply unit 61 (high-frequency energy supply unit), and a control unit 62 for controlling them. The control unit 62 can control the supply of an ultrasonic current generated by the ultrasonic current supply unit 33 and the supply of a high-frequency current generated by the high-frequency current supply unit 61. When the operation button 28 is operated by the operator, an electric signal is transmitted to the control unit 62, and input of an energy operation is detected. Accordingly, the control unit 62 supplies the ultrasonic current from the ultrasonic current supply unit 33 to the vibration transmission member 23 and supplies the high-frequency current from the high-frequency current supply unit 61 to the vibration transmission member 23.

A description will be given of an operation of the medical device of the present embodiment with reference to FIG. 2.

Where an object to be treated exists, the operator holds a living tissue between the vibration transmission member 23 and the jaw 36 of the clamp arm 18. The operator can move the living tissue as in the case where the living tissue is held with forceps, can widen the gap between living tissues, and can perform various other kinds of treatment. The operator can apply energy to the held living tissue by operating the operation buttons 28. When the second operation button 28B corresponding to the coagulation-incision mode is operated, the vibration transmission member 23 vibrates ultrasonically, so that the thermal energy caused by the frictional motion is applied to the living tissue. At the time, the temperature of the vibration transmission member 23 increases, for example, to 200° C. or higher. Because of this, the living tissue and blood vessel can be incised between the treatment surface of the vibration transmission member 23 and the jaw. Simultaneously with this, a high-frequency current flows to the living tissue between the treatment surface 25 (serving as an electrode) of the vibration transmission member 23 and the jaw 36. Accordingly, the living tissue and blood vessel can be coagulated.

In this manner, two kinds of energy are applied from the vibration transmission member 23 and the jaw 36 in the present embodiment, and the living tissue held between them can be coagulated or incised with high efficiency.

When the first operation button 28A is operated in the state where the living tissue is held between the vibration transmission member 23 and the jaw 36, a high-frequency current flows to the living tissue between the treatment surface 25 (serving as an electrode) of the vibration transmission member 23 and the jaw 36, and electric energy can be applied to the living tissue. Because of this, only the coagulation of the living tissue can be performed.

In the present embodiment, the coating portion 37 having heat insulation property is provided on the opposite surface 43, which is opposite to the grasping surface 42. Even if the operator unintentionally brings the opposite surface 43 into contact with the neighboring tissues, these tissues are prevented from thermal damage.

A description will be given of the manufacturing process of the clamp arm 18 of the present embodiment with reference to FIG. 5 etc. The main portion of the clamp arm 18 can be made by the insert molding in which the conductor 34 is inserted. By this insert molding, the coating portion 37 can be formed around the conductor 34.

To be specific, the conductor 34 is placed at the predetermined position inside a mold 63. Preferably, the conductor 34 and the mold 63 are secured using a pin provided for the mold 63 or the like. After a pair of molds 63 are placed one on the other, a molten resin is injected into the cavity inside the molds 63 from the side of a gate 64. At the time, the gate 64 of the molds 63 is located at the position of the proximal end 48 of the conductor 34 or in the neighborhood of that proximal end 48. By this insert molding, the coating portion 37 is formed on the periphery of the conductor 34 (the first surface 51, the second surface 52 and the surfaces of the side wall portions 56). Since the first through hole 44, the second through hole 45 and the auxiliary through holes 46 are provided in the conductor 34, the resin can flow through those holes, and an excessive resin pressure is prevented from being applied to only one of the surfaces of the conductor 34. As a result, the resin pressure inside the molds 63 is made uniform, and the conductor 34 is prevented from moving inside the molds 63 at the time of injection molding.

After the coating portion 37 is formed on the conductor 34 in the manner mentioned above, the jaw 36 is fixed to the grasping surface 42 of the conductor 34 using the pin 41, thereby completing the clamp arm 18.

According to the first embodiment, the medical member is assembled with the assembly unit, is movable relative to at least part of the assembly unit, and is provided with: a conductor 34 including a plurality of curved portions and through holes extending along a plane P including the plurality of curved portions; and a coating portion 37 integrally formed with the conductor 34 in such a manner as to cover the periphery of the conductor and fill the interior of the through holes.

With this structure, the through holes are provided in the curved portions to which biased pressure tends to be applied when the coating portion 37 is formed, and the coating portion 37 fills the through holes. Therefore, the through holes suppress the biased pressure at the time of molding. Since the conductor 34 is prevented from moving at the time of molding the coating portion 37, the probability of producing defective products can be lowered and the yield of medical members can be improved.

The conductor 34 is provided with the first surface 51 including the grasping surface for grasping a living tissue and the second surface 52 opposite to the first surface 51, and the through holes penetrate both the first surface 51 and the second surface 52. Even if a pressure difference exists between the first surface 51 and the second surface 52, the structure mentioned above permits the pressure on one side to be transmitted to the other side via the through holes. The yield of medical members can be improved by providing a simple structure (through holes) in the conductor 34.

The conductor 34 includes positional shift portions which are shifted from the central axis A of the conductor 34, and the through holes are provided in such a manner as to penetrate the positional shift portions in the thickness direction thereof. With this structure, the though holes serve to eliminate the pressure difference in the positional shift portions where non-uniform pressure tends to be generated at the time of molding the coating portion. Therefore, the conductor 34 is prevented from moving at the time of molding, and the yield of medical members can be improved.

The coating portion 37 is formed of an insulating resin, and the gate 64 used for molding the coating portion 37 is provided at the proximal end portion 48 of the conductor 34, which is opposite to the distal end portion 47. In general, a molded article tends to have burrs in the neighborhood of the gate 64. Although the burrs can be removed using a cutter or the like, minute irregularities may remain on the cut portions. With the structure mentioned above, since the gate 64 is located at the proximal end portion 48, irregularities are prevented from remaining on the coating portion 37 in the neighborhood of the distal end portion 47. Therefore, the external shape and thickness of the coating portion 37 are stable in the neighborhood of the distal end portion 47, with which a fine treatment is performed in a living body. As a result, a medical member with high quality can be provided.

The conductor 34 includes the conduction holes 35, and the conductor 34 is electrically connected to the assembly unit by way of the conduction holes 35 and the shaft 27 inserted through the conduction holes 35. In addition, the conductor 34 is supported such that it is movable relative to at least part of the assembly unit, and the coating portion 37 covers portions which are away from the conduction hole 35.

With this structure, electrical conduction to the assembly unit can be attained through the conduction holes 35, and the coating portion 37 does not hinder the electrical connection between the conductor 34 and the assembly unit.

The conduction holes 35 are provided to extend in a direction intersecting the through holes. With this structure, the conduction holes 35 extend in the direction in which non-uniform pressure is hard to generate at the time of molding (namely, in a direction in which the through holes do not extend). Since non-uniform pressure is not generated in the neighborhood of the conduction holes 35, and the conductor 34 is prevented from moving at the time of molding, the yield of medical members can be improved.

The assembly unit is provided with the shaft unit which receives high-frequency energy transmitted thereto and which constitutes one pole when the high-frequency energy is applied to a living tissue. The conductor 34 constitutes the other pole when the high-frequency energy is applied to the living tissue.

With this structure, a high-frequency treatment is enabled in which high-frequency is applied to a living tissue located between the shaft unit and the conductor 34. The conductor 34 is provided with the opposite surface 43 on the opposite side of the grasping surface 42, and the coating portion 37 is formed of a heat insulating resin and covers at least the opposite surface 43. For example, when a treatment in which high-frequency energy is applied to a living tissue is performed, the temperatures of the shaft unit and the conductor 34 become comparatively high. With the structure of the embodiment, even if the operator unintentionally brings the opposite surface 43 into contact with the neighboring tissues, these tissues are prevented from being thermally damaged.

Preferably, the coating portion 37 should be formed of a resin having electrical insulation property. Where the coating portion 37 has electrical insulation property, a current is prevented from leaking and flowing to the neighboring tissues when the living tissue to be treated is applied with high-frequency energy. Accordingly, a medical member can be provided which causes little damage to the neighboring tissues.

The conductor 34 includes wall portions extending from the distal end portion 47 thereof to the proximal end portion 48 opposite to the distal end portion 47, and depressed portions 56A provided in the respective wall portions and continuously provided from the distal end portion 47 to the proximal end portion 48. Since the depressed portions 56A are provided, a resin can easily flow when the coating portion 37 is molded, and non-uniform resin pressure is prevented.

The conductor 34 is provided with auxiliary through holes 46 which penetrate the respective wall portions and which are located at positions corresponding to the depressed portions 56A. Since the wall portions are provided with the auxiliary through holes 46 in addition to the depressed portions 56A, the resin pressure can be made uniform between the obverse side of each wall portion and the reverse side thereof. Because of this, the yield of medical members can be improved.

Second Embodiment

A medical device of the second embodiment of the present invention will be described with reference to FIGS. 8 to 10. A treatment device 11, an example of the medical device of the second embodiment, differs from that of the first embodiment in terms of the shape of a hand piece 12 employed, but the other features are similar to those of the first embodiment. A description will therefore be given mainly of how the second embodiment differs from the first embodiment. As for the features common to the first embodiment, a description and illustration of them will be omitted. In the present embodiment, one of the two directions parallel to the longitudinal direction C of the vibration transmission member 23 will be referred to as distal direction C1, and the direction opposite to the distal direction C1 will be referred to as proximal direction C2.

Figure 8:
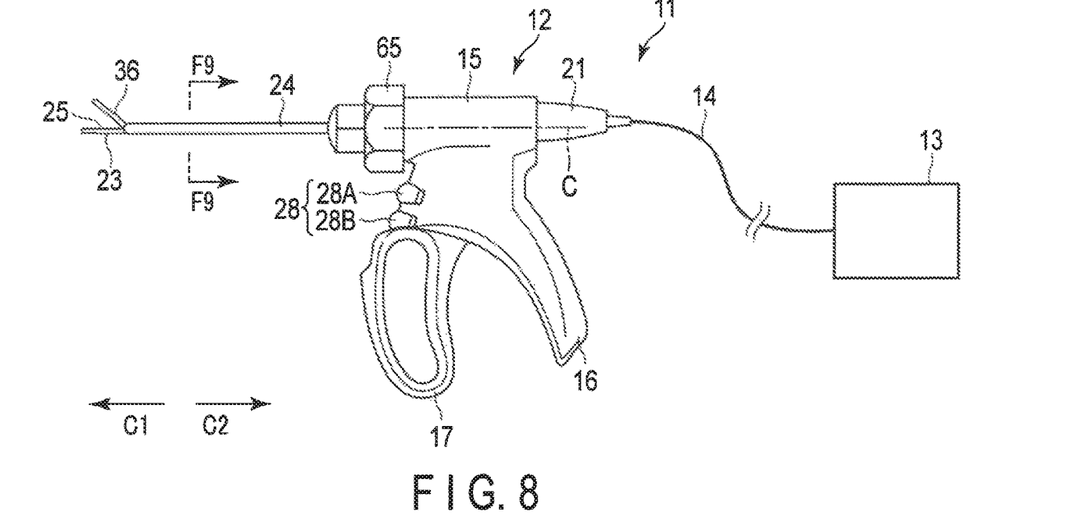
FIG. 8 is a schematic diagram showing the entire structure of a medical device according to the second embodiment.
Figure 9:
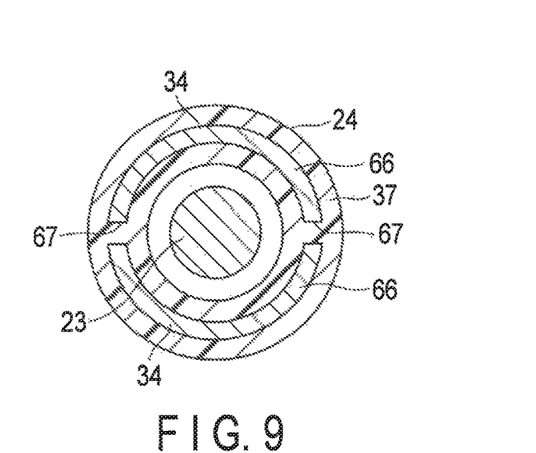
FIG. 9 is a sectional view taken along line F9-F9 of the medical device shown in FIG. 10.

As shown in FIG. 8, the hand piece 12 (assembly unit) is provided with: a resin housing 15 constituting an outer shell; a fixed handle 16 fixed to the housing 15; a movable handle 17 movable relative to the housing 15; a case 21 detachably attached to the housing 15; a vibration generator 22 (transducer) stored in the case 21; a rod-like vibration transmission member 23 (shaft unit; probe) connected to the vibration generator 22; a cylindrical sheath 24 covering the periphery of the vibration transmission member 23 and protecting the vibration transmission member 23; a jaw 36 provided at the distal end portion of the sheath 24 and being rotatable relative to the sheath 24; a cylindrical driving pipe provided inside the sheath 24 and being movable back and forth when the jaw 36 is opened or closed; a knob 65 (rotating knob) fixed to the sheath 24; and a plurality of operation buttons 28 provided on the housing 15. The sheath 24 is an example of a medical member.

The sheath 24 is cylindrical and protects the vibration transmission member 23 located therein. The sheath 24 is attached to the housing 15 such that it is rotatable with reference to the housing 15. The sheath 24 includes, at the distal end portion thereof, a support pin used for rotatably supporting the jaw 36. One of electric wiring lines connected to the power supply unit 13 is connected to the proximal end portion of the sheath 24. The jaw 36 is electrically connected to the sheath 24. Therefore, the jaw 36 at the distal end portion of the sheath 24 serves as one of the poles of the bipolar electrode for bipolar treatment. The vibration transmission member 23 is connected to the other one of the electric wiring lines connected to the power supply unit 13, and serves as the other pole of the bipolar electrode for bipolar treatment.

Figure 10:
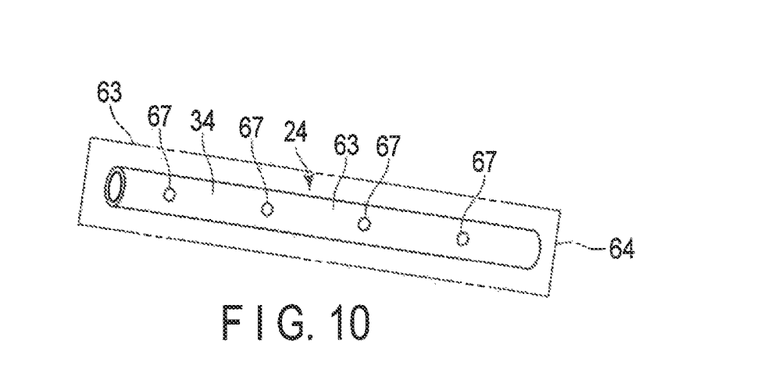
FIG. 10 is a perspective view showing the conductor of the sheath depicted in FIG. 8.

As shown in FIG. 10, the sheath 24 includes a cylindrical conductor 34, and a coating portion 37 covering both the inner peripheral surface and outer peripheral surface of the conductor 34. The coating portion 37 is integral with the conductor 34 and made by insert molding, in which the conductor 34 is inserted. The coating portion 37 is made, for example, of resin (synthetic resin) having electrical insulation property and heat insulation property. The heat insulation property mentioned here means that the coefficient of thermal conductivity is sufficiently smaller than that of the conductor 34 (metal) or the like.

The conductor 34 is an integral member made of stainless steel, for example. The conductor 34 may be made of a copper alloy, an aluminum alloy or another kind of conductive metal. The conductor 34 includes a conductor main body 66 and a plurality of through holes 67 (through hole portions) penetrating the conductor main body 66.

A description will be given of the manufacturing process of the sheath 24 of the hand piece 12 of the present embodiment with reference to FIG. 10 etc.

First of all, the conductor 34 is placed at the predetermined position in a mold 63. Preferably, the conductor 34 and the mold 63 are secured using a pin provided for the mold 63 or the like. After a pair of molds 63 are placed one on the other, a molten resin is injected into the cavity inside the molds 63 from the side of a gate 64. At the time, the gate 64 of the molds 63 is located at the position of the proximal end portion 48 of the conductor 34 or in the neighborhood of that proximal end portion 48. By this insert molding, the coating portion 37 is formed on the periphery of the conductor 34 (the inner peripheral surface and the outer peripheral surface). Since a plurality of through holes 67 are provided in the conductor 34, the resin can flow through these holes, and an excessive resin pressure is prevented from being applied to only one of the outer and inner peripheral surfaces of the conductor 34. As a result, the resin pressure inside the molds 63 is made uniform, and the conductor is prevented from moving inside the molds 63 at the time of mold injection.

After the coating portion 37 is formed on the conductor 34 in the manner mentioned above, the jaw 36 is fixed to the distal end portion of the sheath 24 using the support pin, thereby completing the sheath 24.

According to the present embodiment, even where the medical member is cylindrical, non-uniform pressure is prevented at the time of molding the coating portion 37. Since the conductor 34 is prevented from moving at the time of molding, the yield of medical members can be improved.

The present invention is not limited to the above-described embodiments, and can be modified in various manners in practice without departing from the gist of the invention. In addition, one medical device can be made by properly combining the medical devices of the above embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical member assembled with an assembly unit and being movable relative to at least part of the assembly unit, the medical member comprising:
   a conductor including:
      a plurality of curved portions,
      a first surface including a grasping surface,
      a second surface provided opposite to the first surface,
      a first through hole extending along a plane including the plurality of curved portions, the first through hole penetrating the first surface and the second surface along a penetration axis,
      a conduction hole provided to extend in a direction intersecting the first through hole, the first through hole being provided nearer to a proximal end than the conduction hole is, and
      a positional shift portion which is shifted from a central axis of the conductor, and the first through hole penetrates the positional shift portion in a thickness direction, the thickness direction being perpendicular to a longitudinal axis and perpendicular to the first surface including the grasping surface;
   a coating portion integrally formed with the conductor such that the coating portion covers a periphery of the conductor and fills an interior of the first through hole.

2. The medical member according to claim 1, wherein the conductor is electrically connected to the assembly unit by way of the conduction hole and a shaft inserted through the conduction hole, the conductor is supported such that the conductor is movable relative to at least part of the assembly unit.

3. The medical member according to claim 2, wherein the coating portion is formed of a heat insulating resin and covers at least the second surface.

4. The medical member according to claim 1, wherein the coating portion is formed of an insulating resin, and the conductor is configured to receive a gate used for molding the coating portion, the gate being provided near a proximal end portion of the conductor, which is opposite to a distal end portion of the conductor.

5. The medical member according to claim 4, wherein the conductor includes: a wall portion extending from the distal end portion of the conductor to the proximal end portion thereof, which is located opposite to the distal end portion; and a depressed portion provided in the wall portion and continuously provided from the distal end portion to the proximal end portion.

6. The medical member according to claim 5, wherein the conductor is provided with an auxiliary through hole which penetrates the wall portion at a position corresponding to the depressed portion.

7. The medical member according to claim 1, wherein the conductor is electrically connected to the assembly unit by way of the conduction hole and a shaft inserted through the conduction hole, the conductor is supported such that the conductor is movable relative to at least part of the assembly unit, the coating portion covers those portions which are away from the conduction hole.

8. The medical member according to claim 1, wherein the assembly unit comprises a shaft unit which receives high-frequency energy transmitted thereto and constitutes one pole when high-frequency energy is applied to a living tissue, the conductor constitutes another pole when the high-frequency energy is applied to the living tissue.

9. A medical device comprising a medical member as defined in claim 1.

10. The medical member according to claim 1, wherein the conductor further includes a second through hole extending along the plane and penetrating the first surface and the second surface, the second through hole being formed at a position nearer to the proximal end than the grasping surface is, the coating portion further fills and interior of the second through hole.

11. The medical member according to claim 10, wherein the conductor is electrically connected to the assembly unit by way of the conduction hole and a shaft inserted through the conduction hole, the conductor is supported such that the conductor is movable relative to at least part of the assembly unit, and the conduction hole is provided between the first through hole and the second through hole.

12. The medical member according to claim 1, wherein a jaw is fixed to the grasping surface by means of a pin.

13. The medical member according to claim 1, the conductor further including a wall portion that includes depressed portions that extend from a proximal end portion to a distal end portion.

* * * * *